US005718671A

United States Patent [19]

Bzoch

[11] Patent Number: 5,718,671

[45] Date of Patent: Feb. 17, 1998

[54] SHOULDER, ELBOW, WRIST AND HAND ORTHOSIS

[75] Inventor: Jan J. Bzoch, South Pasadena, Fla.

[73] Assignee: Orthosis Corrective Systems Corp., Pinellas Park, Fla.

[21] Appl. No.: 816,495

[22] Filed: Mar. 13, 1997

Related U.S. Application Data

[63] Continuation of Ser. No. 516,396, Aug. 17, 1995, abandoned.

[51] Int. Cl.[6] .............. A61F 5/00

[52] U.S. Cl. .............. 602/20; 128/878; 5/646

[58] Field of Search .............. 128/845, 877–879, 128/881, 882; 602/4, 5, 12, 16, 19–21, 23; 5/630, 633, 635, 621, 623, 646–648

[56] References Cited

U.S. PATENT DOCUMENTS

| | | | |
|---|---|---|---|
| 1,340,630 | 5/1920 | Maddox | 602/4 |
| 2,614,558 | 10/1952 | Lovell | 602/20 |
| 3,528,413 | 9/1970 | Aydt | 602/16 |
| 4,237,873 | 12/1980 | Terry et al. | 602/20 |
| 4,259,949 | 4/1981 | Axelsson . | |
| 4,576,351 | 3/1986 | Brink | 602/20 X |
| 4,784,120 | 11/1988 | Thomas | 602/20 |
| 5,231,998 | 8/1993 | Rosen et al. | 602/20 X |
| 5,487,724 | 1/1996 | Schwenn | 602/5 X |

*Primary Examiner*—Linda C. Dvorak

*Attorney, Agent, or Firm*—Larson & Larson, P.A.; James E. Larson

[57] ABSTRACT

An orthosis has a clamp designed to clamp the orthosis to the arm of a chair. Adjustment devices incorporated in the orthosis permit adjustment of the position and orientation of the orthosis in all degrees of freedom and the arm rest of the orthosis includes structure allowing an elbow receiving portion to be lengthened or shortened.

11 Claims, 4 Drawing Sheets

SHOULDER, ELBOW, WRIST AND HAND ORTHOSIS

This application is a continuation of U.S. Ser. No. 08/516,396, filed Aug. 17, 1995, now abandoned.

BACKGROUND OF THE INVENTION

The present invention relates to a shouldered elbow, wrist and hand orthosis. In the prior art, orthoses are known and are used as permanent bandages or supports for damaged body parts. U.S. Pat. No. 4,259,949 to Axelsson teaches an orthosis which may be attached to the arm rest of a chair. However, Axelsson fails to teach all of the features and aspects of the present invention including the adjustment means for adjusting the position and orientation of the orthosis with respect to the arm rest in all degrees of freedom.

MMAR Medical Group, Inc. of Houston, Tex. sells an orthosis including a bracket designed to allow releasable affixing of the orthosis to a wheelchair frame. A similarly attachable device is sold by Orthotic Rehabilitation Products, Inc. of Tampa, Fla.

None of these devices teaches all of the features and aspects of the present invention.

SUMMARY OF THE INVENTION

The present invention relates to a shoulder, elbow, wrist and hand orthosis. The present invention includes the following interrelated objects, aspects and features:

(A) In a first aspect, the inventive orthosis includes a clamping mechanism designed to permit clamping of the orthosis to the arm rest of a chair. In the preferred embodiment, the clamping mechanism includes a U-shaped clamp member placeable over the arm rest and a pivotable locking member designed to be manipulated under the arm rest and to be clamped to the U-shaped clamp member to capture the arm rest therewithin.

(B) The U-shaped clamp member has a fitting rotatably attached thereto with a set screw extending through the U-shaped clamp member and having an end engageable with the fitting to lock the fitting in any particular rotative orientation with respect to the U-shaped clamp member.

(C) The fitting has an elongated leg pivotably attached thereto at a pivot which incorporates a locking mechanism designed to lock the pivoted position of the elongated leg with respect to the fitting at any one of a plurality of orientations with respect thereto.

(D) At a portion of the elongated leg distal from the fitting, a further fitting is pivotably attached with a locking mechanism being incorporated into the pivot to allow locking of the further fitting with respect to the elongated leg in any one of a plurality of orientations with respect thereto.

(E) An opening in the further fitting rotatably receives a rod which is connected to a mount for a padded rest designed to support the elbow and lower arm of the user. A locking mechanism on the further fitting allows locking of the rotative position of the mount with respect thereto in any one of a plurality of rotative positions.

(F) The padded rest includes first adjustment means designed to allow adjustment of the length of the padded rest in the area of the elbow support thereof and second adjustment means incorporated into the interconnection between the mount and the padded rest allowing slight longitudinal adjustment of the position of the padded rest with respect to the mount.

Accordingly, it is a first object of the present invention to provide a shoulder, elbow, wrist and hand orthosis.

It is a further object of the present invention to provide such a device including means for clamping the device to an arm rest of a chair.

It is a still further object of the present invention to provide such a device including various adjustment means allowing adjustment of the position and orientation of a padded rest thereof with respect to the arm rest of the chair.

It is a yet further object of the present invention to provide such a device including means for adjusting the length of the padded rest.

It is a still further object of the present invention to provide such a device wherein adjustment of the padded rest may be accomplished with respect to the arm rest of a chair in all degrees of freedom.

These and other objects, aspects and features of the present invention will be better understood from the following detailed description of the preferred embodiment when read in conjunction with the appended drawing figures.

SPECIFIC DESCRIPTION OF THE PREFERRED EMBODIMENT

Figure 1:
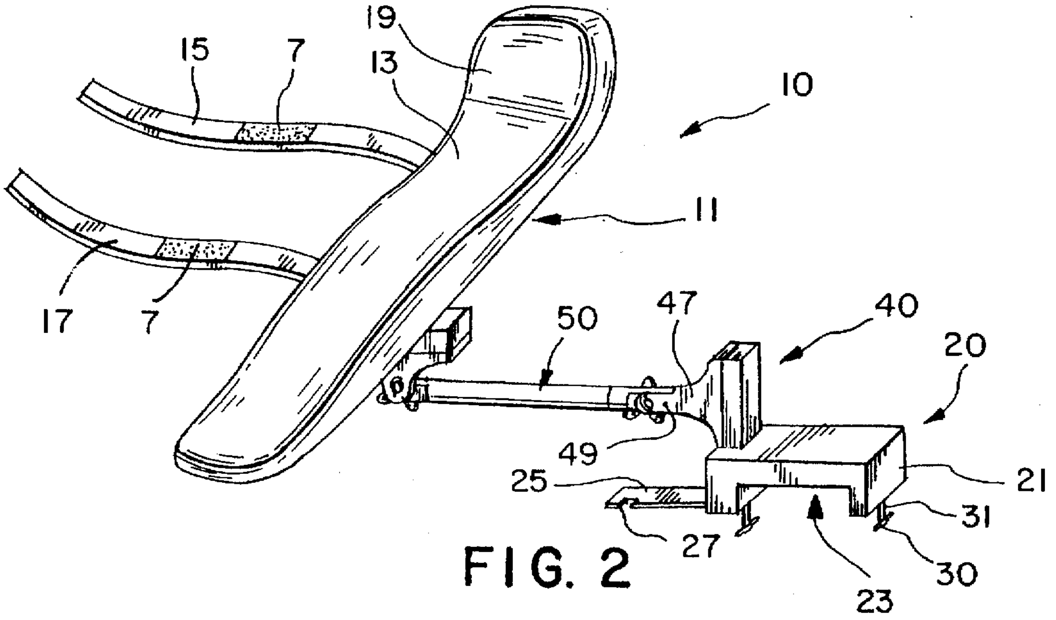
FIG. 1 shows a front perspective view of the present invention.
Figure 2:
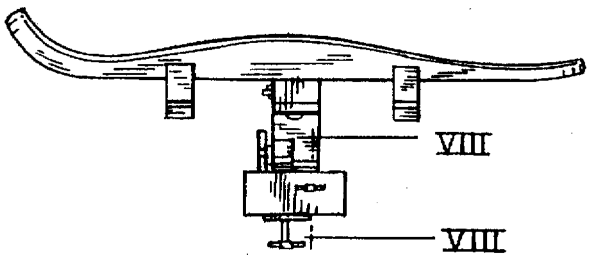
FIG. 2 shows a side view of the present invention.

With reference, first, to FIG. 1, the present invention is generally designated by the reference numeral 10 and includes rest means comprising a padded rest 11 including a cover 13 having straps 15 and 17 designed to wrap around the cover 13 to hold the user's lower arm fastened thereon. The padded rest 11 includes an uplifted portion 19 designed to receive the elbow of the user's arm.

With further reference to FIGS. 1–5, the inventive device 10 includes clamping means consisting of a clamping mechanism 20 which consists of a U-shaped clamp member 21 defining an opening 23, and a pivotable locking member 25 having a notch 27 designed to fit over the stem 31 of a threaded locking pin 30 to allow clamping of the clamping mechanism 20 to, for example, an arm rest 1 (FIG. 3) of a chair (not shown). An additional locking pin 33 extends through an opening (not shown) in the pivotable locking member 25 and is threadably received within a threaded opening (not shown) in the U-shaped clamp member 21.

Figure 8:
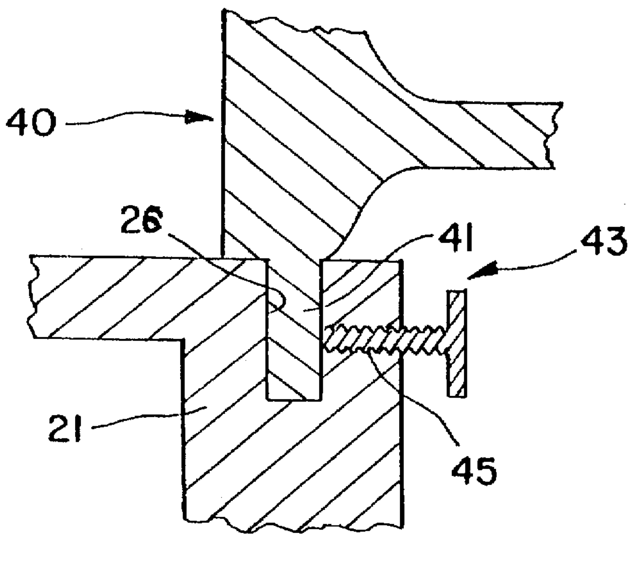
FIG. 8 shows a cross-sectional view along the line VIII—VIII of FIG. 2.

As particularly seen in FIGS. 1, 2, 3 and 4, a fitting 40 is rotatably attached to the U-shaped clamp member 21. With particular reference to FIG. 8, it is seen that the fitting 40 has a depending stem 41 which is rotatably received within an opening 26 formed within the U-shaped clamp member 21. A threaded locking pin 43 is threadably received within a threaded bore 45 in the U-shaped clamp member 21, which bore 45 is generally orthogonal to the opening 26. The locking pin 43 may be loosened whereupon the fitting 40 may be rotated to any desired orientation with respect to the U-shaped clamp member 21, whereupon the locking pin 43 may be tightened against the outer surfaces of the pin 41 to lock the position of the fitting 40 with respect to the U-shaped clamp member 21. If desired, the locking pin 43 may also be employed to lock the vertical position of the fitting 40 with respect to the member 21. In this regard, with reference to FIG. 8, with the locking pin 43 loosened, the pin 41 may be partially removed from the opening 26, adjusted to the desired rotative position and then the locking pin 43 may be tightened to lock the position and orientation of the fitting 40.

Figure 3:
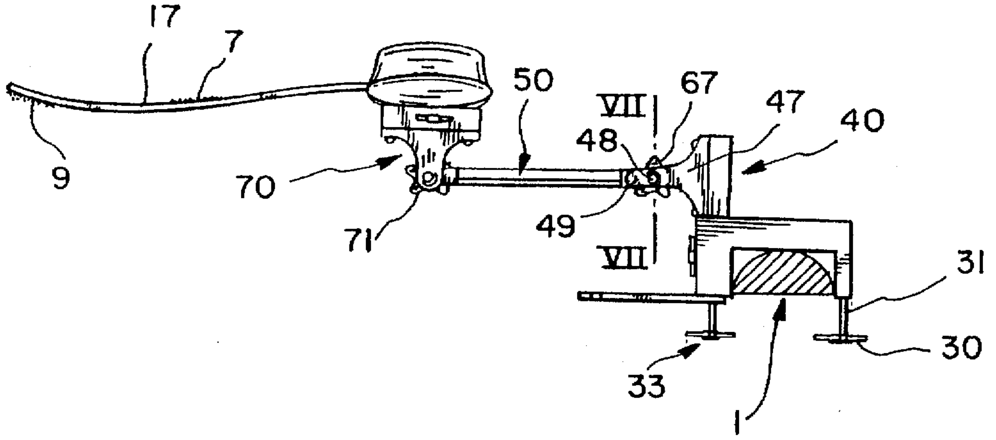
FIG. 3 shows a front view of the present invention with an arm rest of a chair shown within the clamp member thereof.

With reference to FIGS. 1 and 3, the fitting 40 has a laterally extending leg 47 having a proximal end 49 pivotably attached to an elongated leg 50 at a pivot 48.

Figure 6:
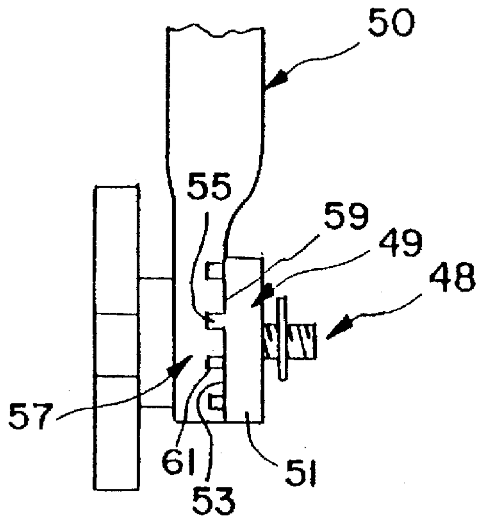
FIG. 6 shows a side view of one of the locking mechanisms of the present invention.
Figure 7:
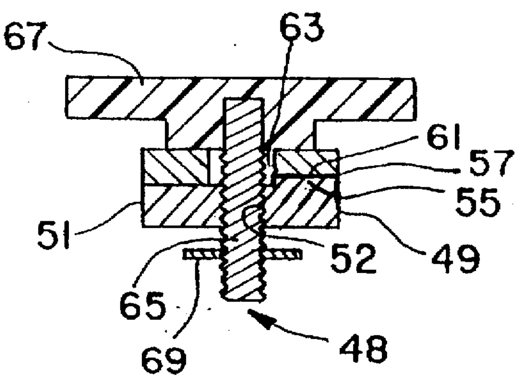
FIG. 7 shows a cross-sectional view along the line VII—VII of FIG. 3, showing further details of the locking mechanism.

With reference to FIGS. 6 and 7, it is seen that the pivot 48 is incorporated into first adjustment means including a locking mechanism designed to allow adjustable pivoting of the leg 50 with respect to the fitting 40 and locking of the relative position of these two elements at any one of a plurality of pre-set orientations. Thus, the end 49 of the leg 47 of the fitting 40 includes a splined member comprising a plate 51 having a flat surface 53 which also includes an outwardly extending spline 55. The end 57 of the leg 50 includes a flat surface 59 abutting the flat surface 53 and having a plurality of spline receiving recesses 61 therein, each of which is sized to receive the spline 55 therein. As particularly seen in FIG. 7, the end 57 of the leg 50 has an opening 63 sized to slidably receive therethrough the threaded stem 65 which is also fixedly attached to the actuator knob 67. The plate 51 has a threaded opening 52 therethrough, sized and configured to threadably receive the threaded stem 65 therethrough. A washer 69 prevents the threaded stem 65 from being unthreaded from the plate 51. When it is desired to adjust the rotative position of the leg 50 with respect to the leg 47, the knob 67 is rotated so that the plate 51 is loosened from the end 57 of the leg 50 allowing the spline 55 to be released from the recess 61 within which it is captured. Thereafter, the leg 50 may be rotated with respect to the leg 47 until the spline 55 lines up with another one of the spline receiving recesses 61 whereupon the knob 67 may be rotated to tighten the end 57 of the leg 50 with respect to the plate 51 to lock the position of the leg 50 with respect to the leg 47.

Figure 4:
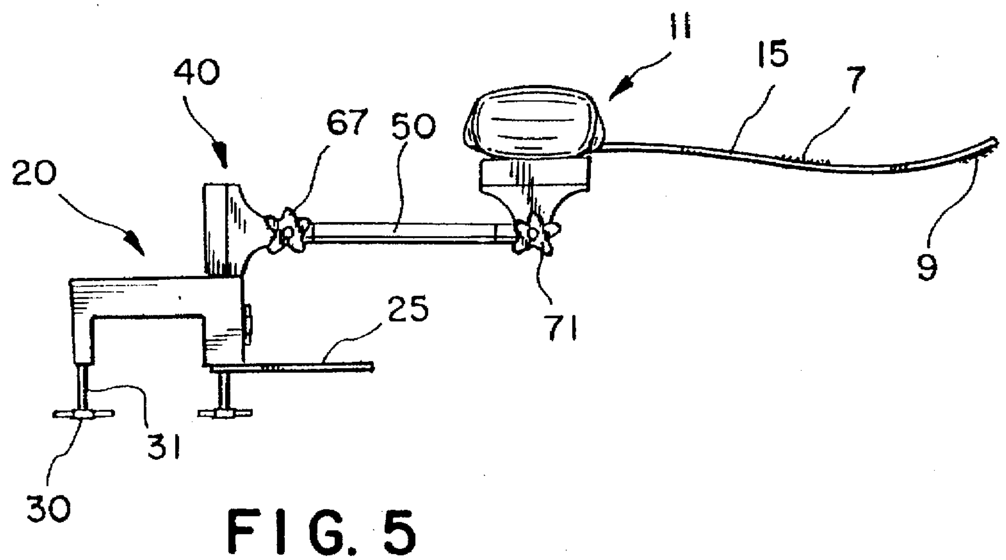
FIG. 4 shows a rear view of the present invention.
Figure 5:
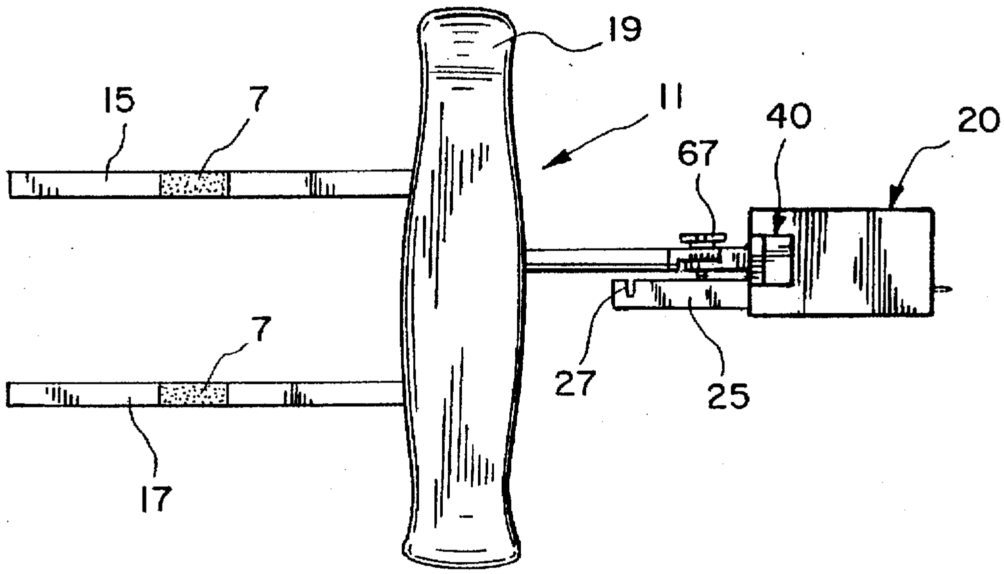
FIG. 5 shows a top view of the present invention.

With further reference, in particular, to FIGS. 3 and 4, at the end of the leg 50 distal from the leg 47, a further fitting 70 is provided and is pivotably attached to the leg 50 at the pivot 71. A mechanism such as that which is particularly illustrated in FIGS. 6 and 7 is also employed with respect to the pivot 71 to comprise second adjustment means allowing adjustment of the rotative orientation of the further fitting 70 with respect to the leg 50 in the manner explained hereinabove concerning the pivot 48. The mechanism permits adjustment of the rotative position of the further fitting 70 in the clockwise and counterclockwise directions in the views of FIGS. 3 and 4 with respect to the leg 50.

Figure 9:
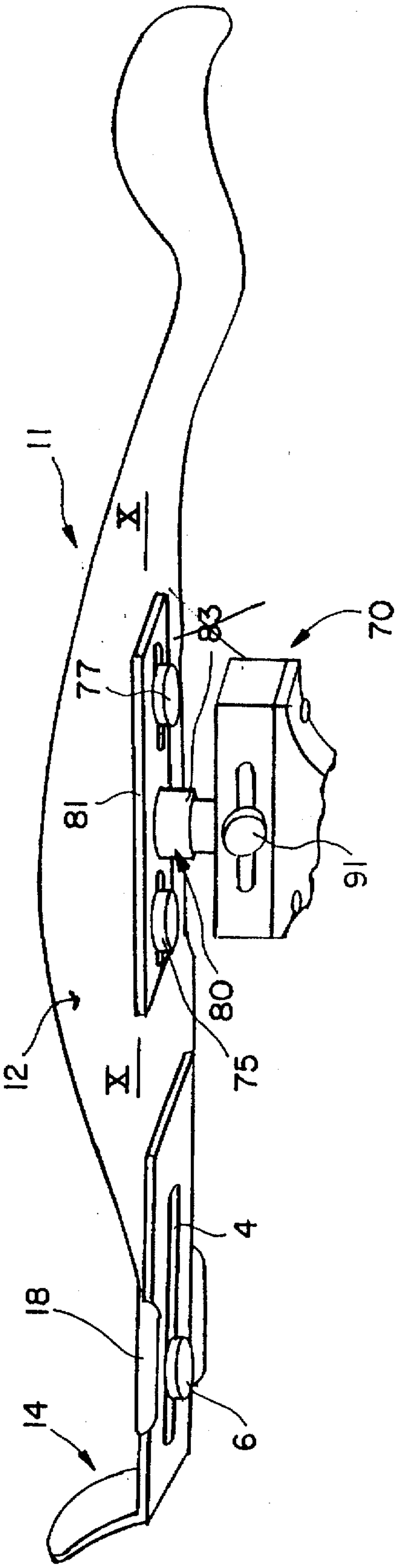
FIG. 9 shows a perspective view looking upwardly from beneath the padded rest of the present invention, with the cover thereof removed to show detail.
Figure 10:
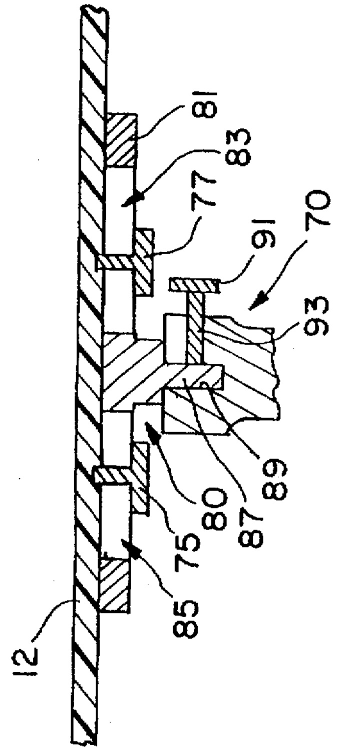
FIG. 10 shows a cross-sectional view along the line X—X of FIG. 9.

With reference to FIGS. 9 and 10, it is seen that the padded rest 11 includes a rigid, preferably plastic frame 12 which is covered by the padded cover 13 best seen in FIG. 1. Locking pins 75 and 77 are threadably received within threaded openings formed in the underside of the rigid frame 12.

With reference to FIG. 9, it is seen that a mount 80 includes a plate 81 rigidly attached to a mounting member 82. As seen in FIG. 10, the plate 81 has elongated slots 83 and 85 designed to slidably receive the locking pins 77 and 75, respectively, therethrough. As best seen in FIG. 9, the heads of the locking pins may bear against the surfaces of the plate 81 adjacent the slots 83 and 85 to allow locking of the position of the plate 81 with respect to the frame 12. Of course, if desired, the pins 75 and 77 may be replaced with threaded rods (not shown) embedded in the undersurface of the frame 12 and discs (not shown) having openings threaded in complementary fashion to the threaded rods, which discs would bear against the surfaces of the plate 81 adjacent the slots 83 and 85 when rotated on the rods. With reference to FIG. 10, the mount 80 includes a depending rod 87 rotatably received within an opening 89 in the fitting 70. A locking pin 91 is threadably received within an orthogonal opening 93 formed within the fitting 70 and may be rotated to a position frictionally bearing against the surfaces of the rod 87 to lock the rotative position of the mount 80 with respect to the fitting 70.

With further reference to FIG. 9, it is seen that the frame 12 includes a main body as well as an adjustable elbow rest 14 including an elongated slot 4 through which a locking pin 6 may extend and may be threadably received within an opening (not shown) in the frame 12 main body so that the elbow rest 14 may be extended to a desired position and may be locked in that position through the use of the locking pin 6. Again, the pin 6 may be replaced with a threaded rod (not shown) embedded in the undersurface of the elbow rest 14 with a disc with an opening threaded in complementary fashion to the rod and designed to bear against undersurfaces of the rest 14 adjacent the slot 4. A depending tab 18 on the frame 12 main body maintains alignment of the elbow rest 14 with respect to the main body.

As seen in FIGS. 1 and 3, the straps 15 and 17 have fastening means 7 thereon comprising one-half of a hook and pile fastening means. As seen in FIG. 3, the other half 9 of the hook and pile fastening means may be located at the end of an opposite face of the straps 15 and 17. In this way, the straps 15 and 17 may be employed to wrap about the lower arm of the user and to firmly fasten the lower arm of the user to the padded rest 11.

With the present invention having been described in great detail, an explanation will now be given of the intended mode of operation.

First, the clamping mechanism 20 is suitably clamped over the arm 1 of a chair which could, if desired, be a wheelchair or any other kind of chair, for that matter. The pivotable locking member 25 is pivoted to a position capturing the arm 1 within the opening 23 in the U-shaped clamp member 21 and the locking pins 30 and 33 are tightened to fasten the pivotable locking member 25. Thereafter, the pin 43 is loosened to allow pivoting of the fitting 40 with respect to the member 21 to a desired rotative position and, if desired, to a desired position of elevation with respect thereto.

Thereafter, the locking mechanism illustrated in FIGS. 6 and 7 is operated to allow adjustment of the angular orientation of the leg 50 with respect to the leg 47 of the fitting 40. Thereafter, the corresponding locking mechanism at the other end of the leg 50 may be operated to adjust the angular position of the further fitting 70 with respect to the leg 50. Thereafter, the locking pin 91, 93 may be manipulated to allow adjustment of the rotative position of the mount 80 with respect to the further fitting 70. Adjustments may also be made concerning the frame 12 and the elbow support 14 as explained above. Of course, these adjustments may be made in the order described hereinabove or in any desired order, since each adjustment is independent of the other adjustments and is not dependent upon the other adjustments.

With the inventive device 10 so clamped to the arm 1 of a chair and with all of the adjustments made as desired, the user may sit in the chair and may rest their arm on the padded rest 11 with the elbow adjacent the portion 19 thereof. Thereafter, the straps 15 and 17 may be extended over the lower arm of the user and may be fastened about themselves to firmly fasten the user's lower arm thereto.

As such, an invention has been disclosed in terms of a preferred embodiment thereof which fulfills each and every one of the objects of the present invention as set forth hereinabove, and provides a new and useful shoulder, elbow, wrist and hand orthosis of great novelty and utility.

Of course, various changes, modifications and alterations in the teachings of the present invention may be contemplated by those skilled in the art without departing from the intended spirit and scope thereof.

As such, it is intended that the present invention only be limited by the terms of the appended claims.

I claim:

1. An orthosis, comprising:

a) a U-shaped clamp for releasably clamping said orthosis to a fixed object; a pivotable locking member adapted to be manipulated under the fixed object and attached to the U-shaped clamp to capture the fixed object therewithin;

b) a frame and padded cover for supporting a forearm of a user;

bb) a first adjustment fitting rotatably attached at a first end to the U-shaped clamp, with an end of the U-shaped clamp engageable with the first end of the first adjustment fitting to lock the first adjustment fitting in a desired rotative orientation with respect to the U-shaped clamp member;

c) a one piece elongated leg pivotably attached at a first end to a second end of the first fitting, with a locking mechanism adapted to lock a pivoted position of the elongated leg with respect to the fitting;

d) a second adjustment fitting interposed between a second end of said elongated leg and a mount for said frame and padded cover, the mount supporting the frame and padded cover rotatably received by said second adjustment fitting whereby said frame and padded cover may be rotatably adjusted with respect to said elongated leg.

2. The orthosis of claim 1, wherein said frame includes a main body and an elbow rest attached to said main body, said elbow rest being adjustably extensible with respect to said main body.

3. The orthosis of claim 1, wherein said first adjustment fitting includes a depending stem rotatably received within an opening formed within the first end of the U-shaped clamp, a threaded locking pin threadably received within a threaded bore in the U-shaped clamp to tighten against an outer surface of the stem to lock it in a desired orientation of said first adjustment fitting with respect to said U-shaped clamp.

4. The orthosis of claim 1 wherein the leg first end is locked to the second end of the first fitting with a locking mechanism consisting of a first splined member and a second member having spline receiving recesses, said member being rotatably adjustable with respect to one another and lockable at any one of a multiplicity of relative rotative orientations.

5. The orthosis of claim 1, wherein said second adjustment fitting includes locking means for locking a desired orientation of said frame and padded cover with respect to said leg.

6. The orthosis of claim 5, wherein said locking means comprises a first splined member and a second member having spline receiving recesses, said members being rotatably adjustable with respect to one another and lockable at any one of a multiplicity of relative rotative orientations.

7. The orthosis of claim 1, wherein said padded cover includes at least one strap adapted to fasten a user's arm thereto.

8. The orthosis of claim 7, wherein said at least one strap comprises two straps.

9. The orthosis of claim 8, wherein each of said straps carries hook and pile fastening means.

10. The orthosis of claim 1, wherein said frame is made of plastic.

11. An orthosis, comprising:

a) a U-shaped clamp for releasably clamping said orthosis to an arm of a patient's chair;

b) rest means including a frame and padded cover for supporting a forearm of the patient;

c) a one piece elongated leg interposed between said U-shaped clamp and said rest means;

d) a first adjustment fitting for adjusting an orientation of a first end of said elongated leg with respect to said U-shaped clamp;

e) a second adjustment fitting for adjusting an orientation of said rest means with respect to a second end of said elongated leg;

f) the first adjustment fitting interposed between said leg and said U-shaped clamp having a depending stem rotatably mounted in a bore of said U-shaped clamp whereby adjustment of rotative position of said first adjustment fitting with respect to said U-shaped clamp may be permitted;

g) the second adjustment fitting interposed between said leg and said rest means, supporting a mount rotatably received by said second fitting whereby said rest means may be rotatably adjusted with respect to said leg;

h) said frame including a main body and an elbow rest attached to said main body, said elbow rest being adjustably extensible with respect to said main body;

i) said first adjustment fitting including locking means for locking a desired orientation of said leg with respect to said U-shaped clamp; and j) said second adjustment fitting including locking means for locking a desired orientation of said rest means with respect to said leg.

* * * * *